United States Patent
Zakoshansky et al.

(10) Patent No.: US 8,013,191 B2
(45) Date of Patent: Sep. 6, 2011

(54) METHOD FOR REMOVING IMPURITIES FROM PHENOL

(75) Inventors: Vladimir Mikhailovitch Zakoshansky, Long Grove, IL (US); Irina Ivanovna Vassilieva, St. Petersburg (RU); Yuri Nikolaevich Koshelev, St. Petersburg (RU); Yuri Ivanovitch Malov, St. Petersburg (RU)

(73) Assignee: Illa International, LLC, Reno, NE (US)

( * ) Notice: Subject to any disclaimer, the term of this patent is extended or adjusted under 35 U.S.C. 154(b) by 104 days.

(21) Appl. No.: 11/489,211

(22) Filed: Jul. 19, 2006

(65) Prior Publication Data

US 2008/0021249 A1    Jan. 24, 2008

(51) Int. Cl.
*C07C 29/74* (2006.01)
(52) U.S. Cl. ........................................ 568/810
(58) Field of Classification Search ................... 568/810
See application file for complete search history.

(56) References Cited

U.S. PATENT DOCUMENTS 3,862,244 A * 1/1975 Genod et al. ................. 568/754
5,502,259 A * 3/1996 Zakoshansky et al. ....... 568/754

FOREIGN PATENT DOCUMENTS

GB   1121595   * 7/1968
RU   2266275 C1 * 12/2005

* cited by examiner

*Primary Examiner* — Shailendra Kumar
(74) *Attorney, Agent, or Firm* — Edward Etkin, Esq.

(57) ABSTRACT

A two-step method of crude phenol treatment from impurities, wherein a first step comprises oxidizing hydroxyacetone and aldehydes impurities, in phenol medium by air oxygen with the use of a heterogeneous catalyst which contains transition metals, and a second step comprises treating the unoxidized impurities with the use of a heterogeneous acidic catalyst. The separation of treatment by-products compounds produced during said phenol treatment may then be carried out by a conventional fractionation, distillation, or equivalent method, to produce highly purified product phenol.

22 Claims, 3 Drawing Sheets

METHOD FOR REMOVING IMPURITIES FROM PHENOL

FIELD OF THE INVENTION

This invention relates to the production of phenol by a cumene method, and in particular, to the method of treating phenol from impurities (carbonyl-containing and unsaturated impurities), with the objective of producing phenol of a sufficiently high purity to satisfy even the most severe process goals.

BACKGROUND OF THE INVENTION

In recent years, the "cumene method" has become the basis for the core technology utilized in the majority of commercial processes for phenol production. Typically, the cumene method includes chemical stages of isopropyl benzene (cumene) oxidation into cumene hydroperoxide (CHP), and further decomposition into phenol and acetone (with the use of acidic catalyst). Chemical characteristics of phenol production process by cumene method determine the contents of a number of chemical compounds being generated as byproducts and appearing in the end product as impurities.

The most common impurities which deteriorate the desirable application properties of end-materials produced at successive phenol processing stages are alkylaromatic, unsaturated and carbonyl-containing compounds, such as alpha-methyl styrene (AMS), mesityl oxide (MO), phorone, 2-methylbenzofuran (2-MBF), hydroxyacetone (HA), cresols, and so on. By way of example, the following reactions describe several possible ways in which undesirable impurities may form during phenol production, as well as illustrate the directions taken by further conversion reactions:

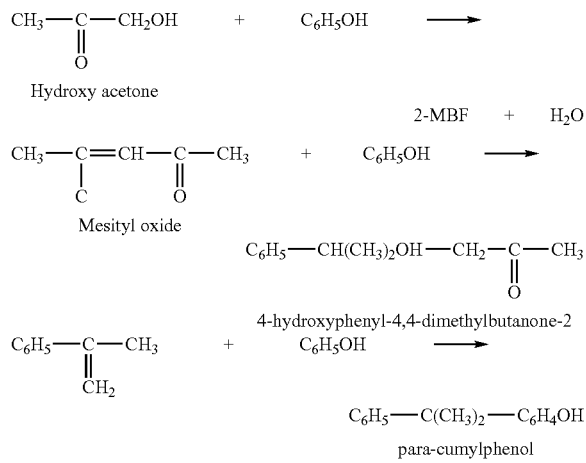

Phenol used in the production of pharmaceuticals and certain polymeric materials must meet high standards with respect to maximum permitted impurity content, which typically does not exceed 0.0100 wt. %. Naturally, such applications require special methods of phenol treatment to eliminate or substantially reduce the presence of undesirable materials in the final phenol product (i.e., impurities, etc.).

Previously known existing approaches to phenol treatment are directed to physical and chemical methods. Physical methods of separation of unwanted compounds commonly encompass fractionation, azeotropic rectification, and extraction, for example as discussed in U.S. Pat. Nos. 2,744,144; 4,532,012; 3,405,038; and 4,504,364.

The main disadvantages of physical methods of phenol treatment, which are widely used in commercial production, are very high energy consumption, and increased sensitivity to volumetric feed rate: increasing of feed rate over a previously established design rate, has an adverse impact on phenol quality.

A vast number of applied chemical methods of phenol treatment are also known. Typically, they are directed to methodologies which rely on chemical properties of compounds which pollute phenol. The most common widely used chemical methods of impurity removal from phenol are demonstrated in the above-shown chemical reactions, with successive rectification-based separation of condensation products (formed during reactions) from phenol. Homogeneous acidic catalysts (for example, see U.S. Pat. No. 3,810,946) and alkaline catalysts (for example, see U.S. Pat. No. 3,335,070) are generally used as catalysts to assist in the reactions.

Another phenol treatment method has been proposed which, together with phenol treatment with alkali (of a pH value reaching 7-9), also uses oxidation by air oxygen (for example, see European Patent No. 1,188,477, and U.S. Pat. No. 3,862,244).

Some of the previously known methods of impurities removal are focused on specific chemical compounds, which have an significant negative impact ion various important quality factors of phenol. Various methods of HA removal serve as an example of this approach. When HA and MBF are derived from phenol using conventional approaches, they impair the color of the phenol product and phenol-based plastic masses. Since it is very important to ensure a required color index, other special methods with different approaches to the solution of the problem have been sought.

The majority of these traditional special methods are based on removal of impurities of HA and MBF from the phenol stream, in which they are accumulated at a CHP cleavage products fractionation stage. This is accomplished by the abovementioned physical methods of aqueous-extractive distillation and extraction, as well as by various chemical methods. In particular, one method of removal of HA from phenol, that consists of conversion of HA into heavy nitrogenous compounds by adding high-molecular amines, is described in U.S. Pat. Nos. 3,322,651 and 3,692,845.

The main disadvantages of these methods are a high cost of amines, as well as the problems with nitrogenous compounds waste treatment, which carries an adverse environmental impact.

The U.S. Pat. No. 6,066,767 introduced a completely different approach to ensure that the required phenol color index is met at the output, is based on the avoidance of MBF formation at a fractionation stage by means of prior removal of HA from CHP cleavage products by circulating salt aqueous solutions. Within this method, the conversion of the extracted HA and aldehydes into the products of deep condensation at pH value more than 7 is conducted in a separately installed reactor, at a temperature of not higher than 130° C. This method is effective for HA (and therefore MBF) removal, but it requires a multi-step extraction and is capital- and energy-intensive.

Another method, described in U.S. Pat. No. 6,573,408, adopts the '767 Patent approach to HA removal, but it has only a single extraction step at a pH value of 3-6, and the temperature of the aqueous salt solution treatment is increased to 300° C. However, these changes only decrease a degree of extraction of HA from CHP cleavage products and boosts energy consumption of the process so dramatically, that this method becomes economically unjustified.

A method of oxidative (air) conversion of HA was proposed in the Oil Refining and Petrochemistry publication ((Russia), 2000, Issue 12, P. 507-510), and allows substantial savings on investments in the processes based on HA extraction, and further conversion in aqueous salt solution. HA oxidation with the use of an alkaline catalyst, proceeds at a rate approximately 10 times higher than its condensation reaction rates, which makes it possible to reduce the reactor size proportionally. The requirement of multi-step extraction for the full HA removal remains a key disadvantage of this method.

Yet another method of HA removal, disclosed in U.S. Pat. No. 6,576,798 ineffectively combines the known techniques of HA removal by aqueous salt solution (as taught in U.S. Pat. No. 6,066,767), with the use of oxidation for HA conversion in this media (see Oil Refining and Petrochemistry (Russia), 2000, Issue 12, P. 507-510)), where hydrogen peroxide, its salts, and permanganates of alkali metals are recommended to be used as oxidants at pH of 3-6.

It is known that in extraction, phenol and acetone enter the aqueous salt solution together with HA, with the concentration of phenol and acetone being about 10 times higher than the HA content. Accordingly, 96-97% (relat.) of the inorganic oxidant injected into the reactor, is spent for oxidation of these target products, boosting the consumption of expensive materials, and leading to unreasonably high expenses.

The most widely used method in commercial production is phenol treatment from impurities with the use of heterogeneous acidic catalysts, mainly sulfonic ion-exchange resins. An obvious advantage of this method over the ones based on the direct use of acids or alkalis, is that it proceeds without waste water formation. However, the use of sulfo-IER as treatment catalysts has its shortcomings. These catalysts are polymeric materials characterized by low mechanical strength and thermostability. In addition, they are prone to swelling and decrepitating at operation. Also, phenol treatment sulfo-IER catalysts have a limited life time, cannot be regenerated, and must be burned in special incinerators after discharge.

The closest counterpart of this approach, is a method of treating phenol from carbonyl containing and unsaturated compounds which involves the contacting of phenol with zeolite catalyst, i.e. mineral catalysts, for example, promoted aluminosilicates with a pore diameter of over 4 Angstrom, at atmospheric pressure or a pressure at which phenol is in liquid phase, and at a temperature of 120° C. to 250° C. These catalysts have no temperature limits for the considered process, are mechanically strong and can be regenerated by air oxygen with restoration of the initial properties. Unfortunately, zeolite catalysts are not universal in respect of treatment of the whole range of impurities contained in phenol. For example, the treatment of phenol from MO and AMS is quite effective, while MBF is not convertible with the use of zeolite catalysts. Moreover, although HA is contained in phenol as an impurity, it is fully convertible in the presence of zeolite catalyst—its disappearance is followed by MBF formation from HA and phenol interaction.

SUMMARY OF THE INVENTION

The object of the present invention is to develop an effective method of phenol treatment, which would eliminate the abovementioned disadvantages of all previously know approaches to phenol treatment. Advantageously, this goal is met by the inventive two-step method of phenol treatment, where at the first step the impurities in the crude phenol medium are oxidized with air oxygen in conjunction with the use of a heterogeneous catalyst which contains transition metals. At the second step, oxidation products and unoxidized impurities are condensed with a heterogeneous acidic catalyst followed by phenol production by means of distillation.

The various features of novelty which characterize the invention are pointed out with particularity in the claims appended to and forming a part of this specification. For a better understanding of the invention, its operating advantages and specific objects obtained by its use, reference should be had to the accompanying drawings and descriptive matter in which there is illustrated and described a preferred embodiment of the invention.

BRIEF DESCRIPTION OF THE DRAWINGS

In the drawings, wherein like reference characters denote corresponding or similar elements throughout the figure:

FIG. 2A illustrates the first step of the inventive process, and FIG. 2B illustrates the second step thereof.

DETAILED DESCRIPTION OF PREFERRED EMBODIMENTS

Figure 1:
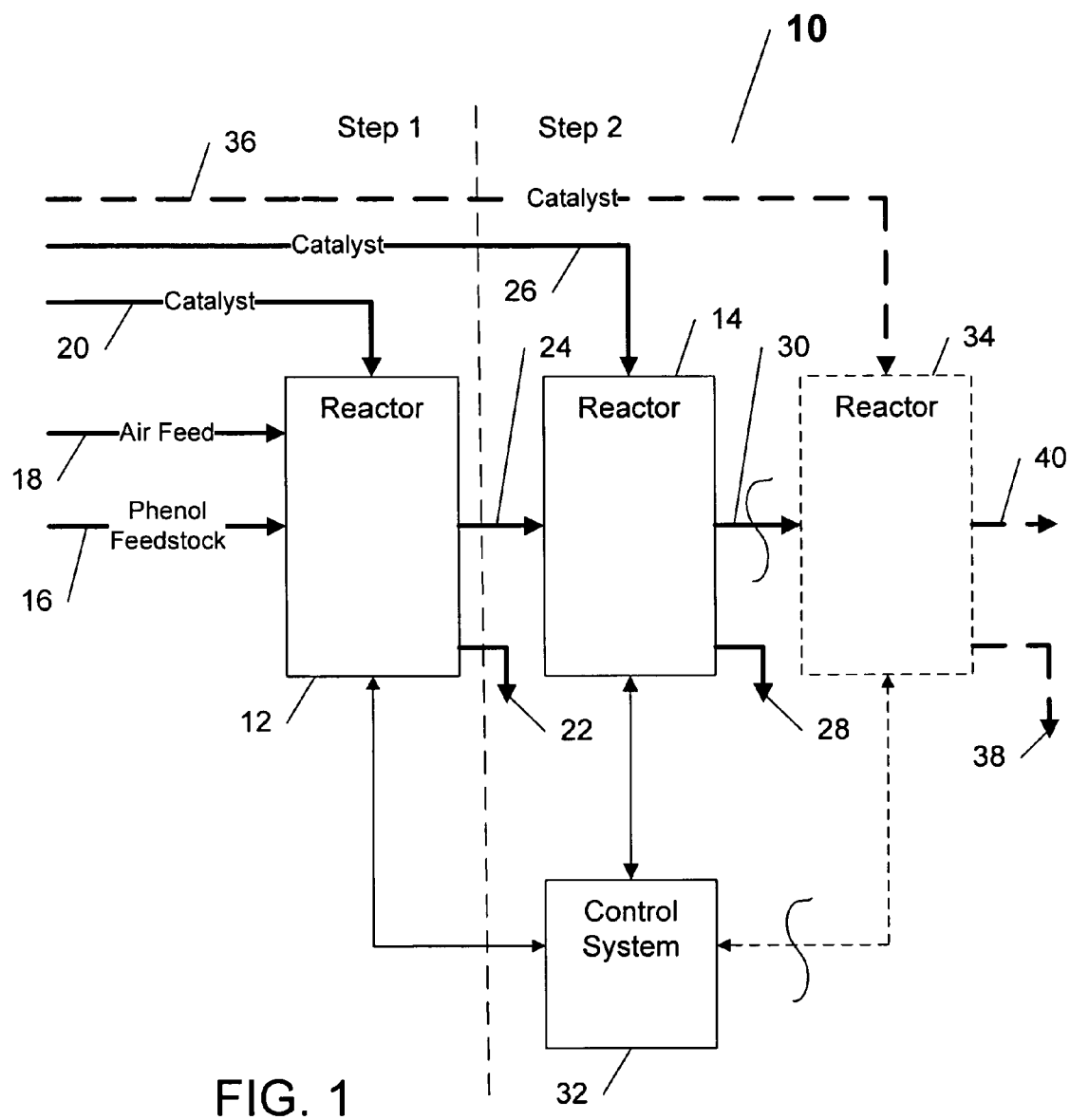
FIG. 1 is a block diagram of a first embodiment of the inventive process of treating phenol where at least two reactors are used for two steps of the process.

The object of the present invention is to develop an effective method of phenol treatment, which would eliminate the abovementioned disadvantages of all previously know approaches to phenol treatment. Advantageously, this goal is met by the inventive two-step method of phenol treatment, where at the first step the impurities in the crude phenol medium are oxidized with air oxygen in conjunction with the use of heterogeneous catalyst which contains transition metals. At the second step, impurities that did not react with the first catalyst, are condensed with a heterogeneous acidic catalyst. Then, first step oxidation products, and other impurities treated at the second step, can be readily separated from phenol by any desired means (distillation, rectification, etc.) to produce the final product phenol.

In the inventive method, the process of phenol treatment from impurities is conducted in a two-step manner in one or more (preferably two) reactors, utilizing heterogeneous catalysts of different types at each step, and at different operating conditions, as described in more detail below.

One of the main challenges in treatment of crude phenol is the sheer number of different impurities/byproducts present therein, each reacting differently to any specific attempted treatment methodology. Thus, while one treatment approach may prove effective against a certain type of impurities, the same approach would have no effect on other impurities, or possibly even have certain detrimental effects on the process (e.g., cause unwanted side reactions, generate hazardous byproducts, etc.). The inventive process readily addresses this challenge as described below.

The essence of the present invention is utilization of one type of heterogeneous catalyst in conjunction with air oxygen at the first step of the process to attack one type of phenol impurities (hydroxyacetone and aldehydes), and subsequent utilization of another type of heterogeneous catalyst (having acidic properties) at the second step of the process, to attack all other impurities that were not treated at the first step. As a result, after the second step of the novel process, all types of impurities are in form of treatment by-products that are readily separable from the treated phenol by conventional means, such as rectification.

Specifically, in accordance with the present invention, the first step of the process utilizes a heterogeneous catalyst that contains transition metals—i.e., metals of variable valency, that change their valency as a result of contact with hydroxyacetone (HA) and aldehydes, and return to their previous valency when the catalyst containing the metals is subjected to air oxygen. Thus, the delivery of air oxygen to the first step of the novel process, brings two very beneficial results: (1) the return of transition metals to their previous valency, which actually regenerates the heterogeneous catalyst and enables its subsequent re-utilization, and (2) oxidation, by air oxygen, on the active centers of the catalyst, HA and aldehydes to products of higher molecularity, which are easy to separate from phenol later in the process (for example, by ordinary rectification). The inventive approach of using a combination of a heterogeneous catalyst containing one or more transition metals and air oxygen to oxidize impurities in crude phenol and prepare them for later separation, advantageously solves the critical challenge of the well-known property of phenol as a very strong inhibitor of oxidation reactions (while also providing regeneration of the utilized catalyst).

The partially treated phenol containing oxidation products of HA and aldehydes, as well as impurities that were not affected, or fully treated, by the first heterogeneous catalyst, are then passed to the second step. Optionally, at least a portion of the partially treated phenol is returned to the first step to repeat treatment with the first heterogeneous catalyst in conjunction with air oxygen.

At the second step of the inventive process, a different heterogeneous catalyst (having acidic properties) is used to treat the remaining impurities, so that at the end of the second step, the resulting product is treated phenol with converted by-products that are easily separable by conventional means. Optionally, at least a portion of the treated phenol is returned to the first step, to the second step, or to both first and second step for additional treatment.

In one embodiment of the inventive method, the difference between the operating conditions at the first and second steps is that at the first step, phenol treatment is conducted at a predefined temperature range temperature range (for example, about 80° C. to about 140° C. or about 90° C. to about 130° C.), with crude phenol medium being delivered thereto, in conjunction with air (at a predetermined air flow rate) with the reaction taking place at a predefined volumetric load (or load range) on the crude phenol medium (for example, ranging from about 0.3 to about 3 $h^{-1}$, or from about 0.5 to about 1.5 $h^{-1}$), while at the second step, the treatment is conducted without air delivery and at a different temperature range, preferably higher than the one at the first step (for example, about 150° C. to about 210° C.).

Figures 2A, 2B:
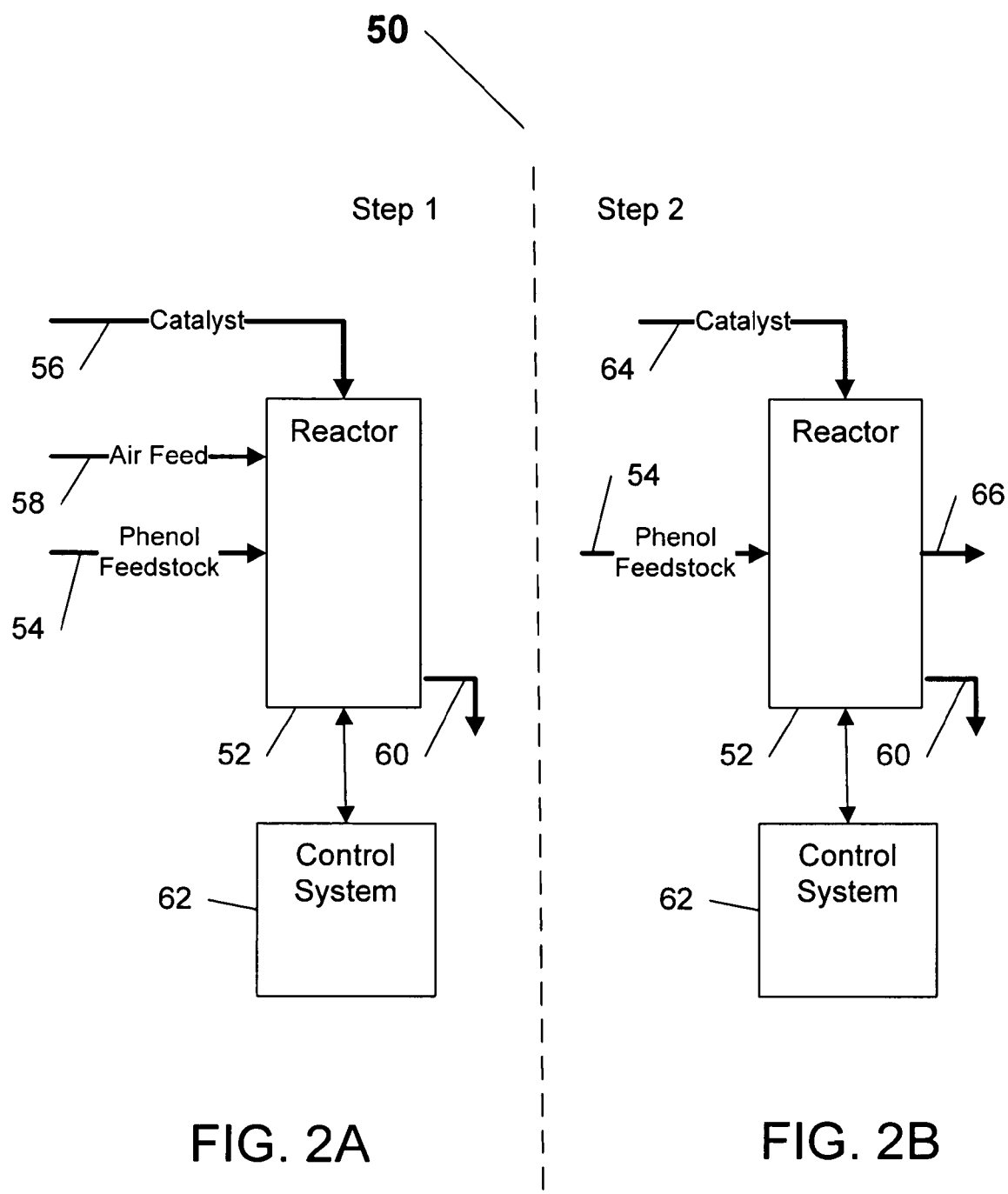
FIGS. 2A and 2B are block diagrams of a second embodiment of the inventive process of treating phenol, in which a single reactor is used for both steps of the inventive process, where

Advantageously, the inventive method may be implemented in one or more reactors, with two reactors (one for each step) being preferable. FIG. 1 shows a first embodiment of the inventive method where two or more reactors are utilized for steps 1 and 2, while FIGS. 2A, 2B show another embodiment of the invention where both steps take place in a single reactor and are chronologically separated.

Accordingly, the first step of treatment under the novel process, results in an oxidative transformation of HA and aldehydes. The second step completes the treatment of phenol from the abovementioned (and other) impurities, utilizing at least one heterogeneous acidic catalyst, prior to conducting final fractionation of crude phenol to produce the desirable pure phenol product.

In both embodiments of the inventive method, as noted above, air is fed at only at the first step (for example, at a rate of about 0.1 $h^{-1}$ to about 80 $h^{-1}$, and preferably from about 1 $h^{-1}$ to about 40 $h^{-1}$). Properly selected operating conditions, described in greater detail below, allow the oxidation reaction of certain impurities (such as HA and aldehydes) with the first heterogeneous catalyst and air oxygen, to be conducted at a rate which is much higher than the rate of reaction between the impurities and phenol. This helps to absolutely exclude MBF formation, and to avoid consequent adverse effects.

Accordingly, at the first step, HA and aldehydes are almost fully converted in the crude phenol medium. Due to the use of the specific indicated types of catalyst, in conjunction with the above-described process operating conditions, the process of HA oxidative transformation takes place in such a manner, as to advantageously prevent MBF formation and phenol oxidation.

The fact that the phenol product obtained after the first step of the inventive treatment contains no HA, avoids the danger of reaching an undesirably high MBF concentration, and facilitates the second step treatment of crude phenol through use of acidic heterogeneous catalysts (such as aluminosilicate catalysts or sulfo-IERs), that in turn enables conversion of other impurities into treatment byproducts that are easily separable from phenol. Accordingly, it is then possible to obtain a phenol product of very high purity after a subsequent conventional rectification stage (or equivalent).

As for the first step, it is preferable to use carbonic sorbents, neutral forms of aluminum oxide and aluminum salts, as well as salts of metals of the main subgroup of group II of the Periodic table as catalyst support. The concentration of the active metal on the support may be 1 to 60 wt. % based on active metal oxide. Total HA conversion at the first step of phenol treatment makes finishing phenol treatment at the second step much easier. To remove remaining concentrations of unsaturated and carbonyl containing compounds at the second step, a wide range of zeolite catalysts and sulfo-IERs may be applied.

Accordingly, at the second step, it is preferable to use aluminosilicate contacts on the base of X or Y type zeolites, whether or not containing promoting or modifying agents. The preferable size of pore entrances of catalysts used at the second step is greater than about 5 Angstroms, or the catalysts may be in a form of ion exchange resins (IERs) of KU-2, KU-23, Amberlyst, Amberlite, Lewatit, Wofatit, or other forms/types. It should be noted that the Russian IERs of KU-2 and/or KU-23 may be readily substituted with any sulfonic acid cation exchange resin catalysts having a general static exchange capacity of at least about 1 mmole/$cm^3$ and working temperature interval of about 80° C. to about 155° C. It is also preferable to use the combination of aluminosilicate contacts on the base of X or Y or other type zeolites, or IERs of KU-2, KU-23, Amberlyst, Amberlite, Lewatit, Wofatit, or other forms types, as catalysts for the second step.

Air flow rate into the reactor may be about 0.1 to about 80 $h^{-1}$, but the most preferable value is about 1 to about 40 $h^{-1}$. In one embodiment of the present invention, the specific air flow rate (or range) is selected preferably based on at least one of: (1) the desirable and/or necessary degree of removal of undesirable hydroxyacetone (HA) from phenol during the inventive process; and (2) the rate needed to produce the required valent state of metals involved in HA oxidation.

In one embodiment of the present invention, at the first step of the novel phenol treatment process, at least one of the following may be readily used as catalysts: metal compounds (preferably oxides) of the secondary subgroups of I group (preferably copper) and VI group (preferably molybdenum), and metals of the VIII group (preferably nickel and cobalt) of the Periodic table on neutral support with minimum number of proton and aprotic acidic sites.

In accordance with the present invention, the supports utilized (when necessary) in conjunction with the heterogeneous catalysts, may be selected from the following: coals, unreactive aluminum hydroxide and magnesia, as well as carbonates, sulfates and phosphates of metals of II and III groups of the Periodic table.

Alternately (and preferably), one particularly advantageous support that may be utilized may be calcium phosphate prepared in a manner such that its crystalline phase is represented predominantly by a substantial quantity of hydroxyapatite. This support and the catalysts based thereon, demonstrate high stability characteristics at the desired phenol treatment process conditions. Moreover, unlike sulfo-IERs, a calcium phosphate—supported catalyst, that has reduced effectiveness as a result of long-term use in commercial operations, may be advantageously regenerated, by steam or oxidative regeneration, to restore its initial properties.

At the conclusion of the first step, steaming is utilized to separate the first catalyst from the phenol product, which was sorbed during process operation, with subsequent treatment of phenolic waters at dephenolation units (not shown in FIGS. 1 and 2A, 2B, but commonly available at phenol plants). Spent and steamed catalyst may be essentially equivalent to natural mineral apatite, and thus does not require special disposal or burial methods (as it is not environmentally hazardous), and also can be treated to recover the active metal promoter (if necessary).

At the second step of phenol treatment, catalysts may be selected from a wide range of materials having acidic properties. For example, second step catalysts may be selected from, but are not limited to, the following:
- medium- and/or wide-pore aluminosilicates (that may be either promoted/modified (e.g., using rare earth elements), or may be free from any promoters or modifiers, and that may be formed with any binding agent, as a matter of design choice),
- aluminosilicates having a composition that includes a certain quantity of zeolites (e.g., about 7% to about 10%),
- zeolites,
- certain asulfo-IERs of various types, and
- sulfuric acid.

In many applications it may be preferable to utilize X or Y type zeolite-based catalysts (zeolites with FAU index of the International Zeolite Association).

Feed space velocity (LHSV) at the first and second steps of treatment is determined by concentration of impurities in phenol, but it usually ranges from 0.2 to 3 $h^{-1}$. Optimum values of feed space velocity at the first and the second steps of phenol treatment may differ due to selected volume of reactors at continuous process conditions.

Referring now to FIG. 1, an exemplary embodiment of the inventive process is shown as a phenol treatment process 10. It should be noted that the for the sake of clarity, the process 10 is illustrated in FIG. 1 as a functional block diagram rather than as an engineering process schematic—the shapes and positions of various lines, their reactor entry points, and absence of typical industrial equipment from the drawing are not meant to demonstrate actual commercial implementation, but rather serve as a basis upon which, one skilled in the art can readily design the appropriate industrial process in accordance with the present invention.

The process 10 is conducted in at least two reactors: reactor 12 for the first step, and reactor 14 for the second step. It should be noted, that more than one reactor can readily be used for each step, as a matter of design choice or convenience. For example, an optional third reactor 34 is shown as being used at the second step in conjunction with the second reactor 14 by way of example only. Phenol feedstock is delivered to the first reactor 12 via feed line 16, along with air oxygen feed 18 and a first step heterogeneous catalyst 20. The first step of the inventive process is then conducted in the reactor 12, at the above-described first step operating/process conditions to oxidize certain impurities into oxidation products (e.g. to substantially convert HA, etc.), to thus produce partially treated phenol that also includes impurities that were not significantly affected by the first step heterogeneous catalyst 20. The partially treated phenol is then transferred to the second reactor 14, via line 24, for step two of the process 10. Optionally, at least a portion of the partially treated phenol may be returned to the feed line 16 via line 22 to repeat the step one treatment (for example, if the step one treatment was not as effective as desired).

The second step of the process 10 is then conducted in the reactor 14 where the second step heterogeneous catalyst 26 is delivered for treatment of the reaction product produced during step one. As noted above, the temperature at which the second reactor 14 is operated, is preferably higher than that of the first reactor 12. Optionally, the various operating/process conditions and other process 10 parameters may be determined and controlled by a control system 32, which may be a computer system or other type of industrial process control system.

When step two of the process 10 is completed, as described above, the remaining impurities are substantially separated from phenol to enable subsequent final fractionation of treated phenol removed through line 30 to produce the desirable pure phenol product (not shown). Optionally, at least a portion of the treated phenol may be returned to the feed line 16, to the line 24, or to both lines 16 and 24, via line 28 to repeat treatment at one or both of the previous steps (for example if the treatment at one or both of the previous steps was not as effective as desired).

As noted above, rather than returning the treated phenol for repeated step one and/or step two treatment, the optional second step two reactor 34 may also be utilized to repeat the second step after reactor 14, if necessary. The reactor 34 may thus be provided with second step catalyst 36, which may be different from the second step heterogeneous catalyst 26 (but still with acidic properties) and where the treated phenol product is sent to final fractionation via optional line 40. As above, optionally, at least a portion of the treated phenol may be returned, via a line 38, to one or more of the previous feed lines 16, 24, and/or 30 to repeat treatment at one or more of the previous steps.

In one embodiment of the present invention, the reaction involving oxidation of certain impurities by air oxygen and the condensation of oxidation products, is conducted in the same reactor, with the use sequential use of two different types of heterogeneous catalysts—i.e. catalysts which contain transition metals at the first step, and catalysts that have acidic properties at the second step. The treatment reactor(s) temperature should be maintained within the range of about 50 to about 250° C.; with the preferable temperature range being about 80 to about 210° C. While the temperature ranges at both steps of the process may be substantially similar or the same, it is preferable to conduct the first step at a temperature lower than at the second step.

Referring now to FIGS. 2A and 2B, by way of example, an exemplary embodiment of the inventive process implemented in a single reactor 52 is shown as a process 50. As noted above, the process 50 also involves two steps, except that the steps are conducted in the same reactor one after another. Otherwise, the process 50 is similar to process 10 of FIG. 1. Thus at the first step (FIG. 2A), phenol feedstock is delivered, via a line 54, to the reactor 52, along with air oxygen feed 58 and a first step heterogeneous catalyst 56. The first step of the inventive process is then conducted in the reactor 52, at the above-described first step operating/process conditions to oxidize impurities into oxidation products (e.g. to substantially eliminate HA, etc.), to produce partially treated phenol. Optionally, at least a portion of the partially treated phenol may be returned to the feed line 54 via line 60 to repeat the step one treatment (for example if the step one treatment was not as effective as desired).

After the operating conditions for the second step are prepared for the reactor 52, the second step of the process 50 is then conducted (FIG. 2B), where the second step heterogeneous catalyst 64 with acidic properties, is delivered for treatment of the impurities in the reaction product of step one that were not affected by the first step heterogeneous catalyst.

As noted above, the reactor 52 may be kept at a higher (or similar) temperature, as at step one, which is preferable. Optionally, the various operating/process conditions and other process 50 parameters may be determined and controlled by a control system 62, which may be a computer system or other type of industrial process control system.

When step two of the process 50 is completed, as described above, the remaining impurities are substantially separated from phenol to enable subsequent final fractionation of treated phenol removed through line 66 to produce the desirable pure phenol product (not shown). Optionally, at least a portion of the partially treated phenol may be returned to the feed line 54 via line 60 to repeat the step two treatment (for example if the step two treatment was not as effective as desired).

Figure 3:
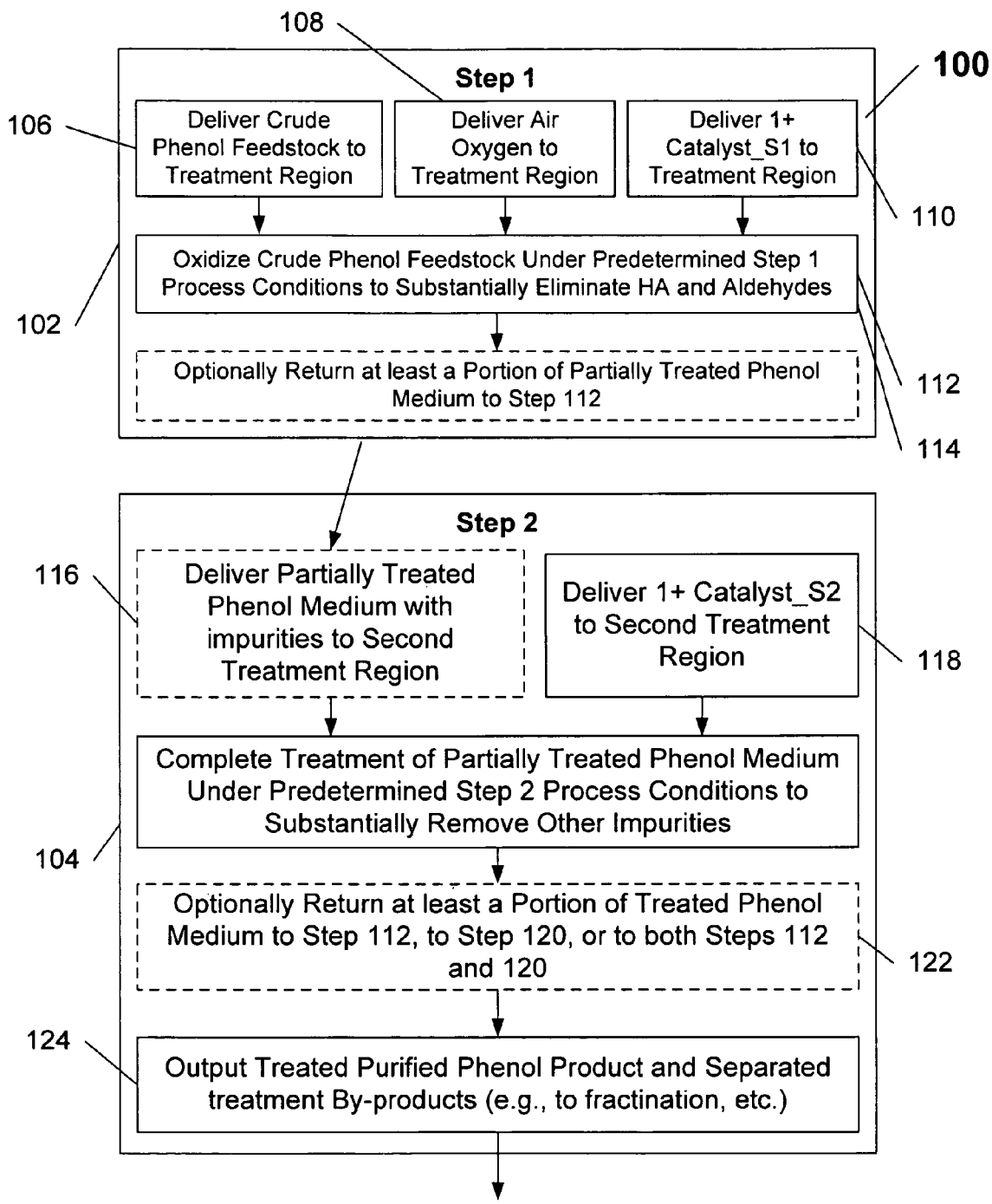
FIG. 3 is a process flow diagram of an exemplary embodiment of the operational steps of inventive processes of FIGS. 1 to 2B.

While, as previously discussed, the novel phenol process may be readily implemented in a variety of embodiments, one exemplary embodiment of the inventive process is shown in FIG. 3, by way of example, as a process 100 that includes illustrates the first step of the novel process with steps 102 to 114, and the second step thereof, with steps 116 to 124. The process 100 provides a helpful illustration of implementation of processes 10 of FIG. 1 and 50 of FIGS. 2A, 2B. The various steps 102 to 124 shown in FIG. 3 are self-explanatory, with the term "Catalyst_S1" referring to step one heterogeneous catalyst containing at least one transition metal, and the term "Catalyst_S2" referring to step two heterogeneous catalyst with acidic properties.

In a two or more reactor configuration of the novel process (e.g., process 10 of FIG. 1), all of the steps 102 to 124 are conducted as shown, including the optional step 116, with the term "treatment region" referring to the reactor(s) of step one, and the term "second treatment region" referring to the reactor(s) of step two. In a single reactor configuration of the novel process (e.g., process 50 of FIGS. 2A, 2B), all of the steps 102 to 124 are conducted as shown, except for the step 116, with the terms "treatment region" and "second treatment region" both referring to the single reactor, with the second treatment region indicating the utilization of the single reactor for the second step of the novel process.

Following are the examples, which describe exemplary implementations of the invented method, but do not limit the inventors' claims.

Example 1

A quantity of 18 g of pestled calcium molybdate was mixed in a kneader with 160 g of powdery disubstituted calcium phosphate, with addition of 50 ml of water, and was plastified for 1 hour. The mass was formed by an extrusion machine, dried for 12 hours at the temperature of 120° C., and calcinated for 3 hours at 350° C.

The prepared catalyst was then placed into a flow-through reactor heated by an electric furnace. The second reactor, similar to the first reaction and placed in series therewith, was filled with zeolite containing catalyst "Zeokar-C10".

Phenol medium, rich in carbonyls and containing unsaturated impurities (the list and concentrations of which are provided below in Table 1), was used as the feed.

The phenol feedstock from a heated vessel was pumped by a metering pump into a mixer for mixing with the air injected into the reactor. Afterward, the air-enriched mixture was fed to the first reactor. The reactor effluent passed through a separator for the separation from air, and liquid phenol was fed into the second reactor. Temperature conditions in the cascade reactors were maintained by electric heating. After cooling, the reaction product was tested by a gas-liquid chromatography method to determine the presence and level of impurities. The content of the feedstock and process conditions, including temperatures in the reactors, feed and air rates, and impurities content in the resulting product, are specified in Table 1, below.

Example 2 (for Comparison)

Phenol treatment was conducted as per Example 1, but the first reactor was switched off, and the feedstock was pumped directly to the second reactor. The content of impurities in the resulting phenol product, for this example, are provided in Table 1, below.

Example 3

The catalyst of the first reactor was prepared in the same way as per Example 1 and phenol treatment was conducted as per Example 1 but the second reactor was filled with sulfo-IER Lewatit. The content of feedstock and process conditions, including temperature ranges in the reactors, feed and air rates, and impurities content in the resulting product, are specified in Table 1, below.

Example 4

The catalyst of the first reactor was prepared in the same way as per Example 1 and phenol treatment was conducted as per Example 1 but the feedstock contained 1000 ppm of HA.

The content of feedstock and process conditions, including temperature ranges in the reactors, feed and air rates, and impurities content in the resulting product, are specified in Table 1, below.

Example 5

The catalyst of the first reactor was prepared in the same way as per Example 1 and phenol treatment was conducted as per Example 1 but the feed space velocity at the first and second steps was 2 hr$^{-1}$.

The content of feedstock and process conditions, including temperature ranges in the reactors, feed and air rates, and impurities content in the resulting product, are specified in Table 1, below.

Example 6

The catalyst was prepared in the same way as per Example 1, but calcium phosphate was replaced by an equal amount of magnesia. In the second reactor, the phenol treatment was conducted as per Example 1.

The content of feedstock and process conditions, including temperature ranges in the reactors, feed and air rates, and impurities content in the resulting product, are specified in Table 1, below.

Example 7

A solution of 305 g of ammonium carbonate (($NH_4$)$_2CO_3$) in 2,000 ml of distilled water was added, in conjunction with continuous mixing for 1 hour, to a solution of 497 g of nickel nitrate (Ni($NO_3$)$_2$×6$H_2O$) in 1,200 ml of water, mixed with 379 g of chromic nitrate (Cr($NO_3$)$_3$×9$H_2O$) in 1,000 ml of water. The sediment was filtered, water-washed, dried for 10 hours at 110 to 120° C. and calcinated for 3 hours at 300° C. A quantity of 8 g of powdered graphite was added to the thoroughly pestled powder. Then, the resulting mass was mixed and formed into pellets in a laboratory extruder. The catalyst was placed into the first reactor, and phenol was treated in the manner similar to Example 1 at various conditions. The content of feedstock and process conditions, including temperatures in the reactors, feed and air rates, and impurities content in the resulting product, are specified in Table 1, below.

Example 8

A solution of 300 g of ammonium carbonate (($NH_4$)$_2CO_3$) in 2,000 ml of distilled water was added into the solution of 302 g of copper nitrate (Cu($NO_3$)$_2$×3$H_2O$) mixed with 69.2 g of chromic nitrate (Cr($NO_3$)$_3$×9$H_2O$), 10.5 g of barium nitrate and 228 g of zinc nitrate (Zn($NO_3$)$_2$×6$H_2O$) in 1,500 ml of distilled water. The sediment was filtered, water-washed, dried for 10 hours at 110 to 120° C. and calcinated for 3 hours at 300° C. A quantity of 8 g of powdered graphite was added to the powder thoroughly pestled powder. Then, the resulting mass was mixed and formed into pellets in a laboratory extruder.

The catalyst was subsequently placed into the first reactor, and phenol was treated in the manner similar to Example 1 at various conditions. The content of feedstock and process conditions, including temperatures in the reactors, feed and air rates, and impurities content in the resulting product, are specified in Table 1, below.

TABLE 1

| | | Example No. | | | | | | | | | | | | | |
|---|---|---|---|---|---|---|---|---|---|---|---|---|---|---|---|
| | | 1 | | | 2 | | | 3 | | | 4 | | | 5 | | |
| Reactor No. | feed | I | II | feed | I | II | feed | I | II | feed | I | II | feed | I | II |
| Feed rate, ml/h: | | 12 | 12 | | 12 | | | 12 | 12 | | 12 | 12 | | 6 | 6 |
| Air flow rate, ml/h: | | 60 | — | | — | | | 60 | — | | 120 | — | | 120 | — |
| Feed space velocity, 1/h | | 1 | 1 | | 1 | | | 1 | 1 | | 1 | 1 | | 2 | 2 |
| Air space velocity, 1/h | | 5 | | | | | | 5 | | | 10 | | | 10 | |
| Temperature, ° C. | | 120 | 200 | | 200 | | | 120 | 120 | | 170 | 90 | | 120 | 200 |
| Content in products, ppm: | | | | | | | | | | | | | | | |
| MO | 110 | 100 | 1 | 110 | | 1 | 110 | 100 | 1 | 110 | 90 | 1 | 110 | 110 | 1 |
| AMS | 390 | 70 | 2 | 390 | | 2 | 390 | 70 | 2 | 120 | 110 | 2 | 120 | 50 | 1 |
| DMBA | 180 | 0 | 0 | 180 | | 0 | 180 | 0 | 0 | 50 | 40 | 0 | 50 | 0 | 0 |
| cumene | 10 | 5 | 4 | 10 | | 4 | 10 | 5 | 4 | 10 | 0 | 0 | 10 | 5 | 3 |
| HA | 480 | 0 | 0 | 480 | | 0 | 480 | 0 | 0 | 1000 | 10 | 0 | 1000 | 2 | 0 |
| 2-MBF | 5 | 5 | 5 | 5 | | 485 | 5 | 5 | 3 | 5 | 5 | 15 | 5 | 5 | 7 |

| | | Example No. | | | | | | | |
|---|---|---|---|---|---|---|---|---|---|
| | | 6 | | | 7 | | | 8 | | |
| Reactor No. | cbIpbe | I | II | cbIpbe | I | II | cbIpbe | I | II |
| Feed rate, ml/h: | | 6 | 12 | | 12 | 12 | | 6 | 6 |
| Air flow rate, ml/h: | | 120 | — | | 60 | — | | 120 | — |
| Feed space velocity, 1/h | | 2 | 1 | | 1 | 1 | | 2 | 2 |
| Air space velocity, 1/h | | 10 | | | 5 | | | 10 | |
| Temperature, ° C. | | 120 | 200 | | 170 | 200 | | 90 | 200 |
| Content in products, ppm: | | | | | | | | | |
| MO | | 110 | 100 | 1 | 110 | 80 | 2 | 110 | 90 | 0 |
| AMS | | 390 | 70 | 3 | 390 | 190 | 1 | 120 | 100 | 0 |
| DMBA | | 180 | 0 | 0 | 180 | 0 | 0 | 50 | 30 | 0 |
| cumene | | 10 | 5 | 0 | 10 | 0 | 0 | 10 | 0 | 0 |
| HA | | 480 | 5 | 0 | 480 | 10 | 0 | 900 | 10 | 0 |
| 2-MBF | | 5 | 5 | 10 | 5 | 5 | 15 | 5 | 5 | 15 |

Thus, while there have shown and described and pointed out fundamental novel features of the invention as applied to preferred embodiments thereof, it will be understood that various omissions and substitutions and changes in the form and details of the devices and methods illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. It is the intention, therefore, to be limited only as indicated by the scope of the claims appended hereto.

We claim:

1. A two-step method for removing, from crude phenol, a plurality of predetermined undesirable impurities comprising at least hydroxyacetone and aldehydes, comprising the steps of:
   (a) at a first step, utilizing a first transitional heterogeneous catalyst comprising a transitional valency metal, in conjunction with air oxygen delivered at a predetermined flow rate, to oxidize, by first transitional heterogeneous catalyst, serving as an oxidizing agent, at least a portion of the plural undesirable impurities, comprising hydroxyacetone and aldehydes, upon contact therewith, by transferring its oxygen content thereto, under first predetermined operating conditions, thereby:
      (1) transforming, by said first transitional heterogeneous catalyst, at least a portion of the first plural undesirable impurities into an oxidation treatment product that is readily separable from phenol, and
      (2) at least partially regenerating said first transitional heterogeneous catalyst by substantially simultaneously regenerating said transitional valency metal thereof by action of air oxygen thereon, such that said transitional valency metal transitions from a lower valency state in which said transitional valency metal lacks oxidation properties, to a higher valency state in which said transitional valency metal comprises catalytic properties and is operable to oxidize the hydroxyacetone and the aldehydes undesirable impurities, upon contact therewith, by transferring its oxygen content thereto; and
   (b) at a second step, utilizing a second heterogeneous catalyst having acidic properties and being different from said first heterogeneous catalyst, to treat remaining unoxidized plural impurities, under second, predetermined operating conditions, to form plural treated byproducts that are readily separable from phenol, to enable subsequent production of desirable purified phenol by removal of said oxidation treatment product and said plural treated byproducts therefrom.

2. The method of claim 1, wherein said step (a) is conducted in a first reactor, and wherein said step (b) is conducted in a second reactor.

3. The method of claim 1, wherein said step (a) and said step (b) are conducted in a single reactor, further comprising the step of:
   (c) after said step (a), and before said step (b), configuring said single reactor for said second predetermined operating conditions.

4. The method of claim 1, wherein said step (a), further comprises the steps of:
   (d) delivering said first transitional heterogeneous catalyst into contact with the crude phenol; and
   (e) delivering air oxygen into contact with the crude phenol and first transitional heterogeneous catalyst at said predetermined air flow rate.

5. The method of claim 4, wherein said predetermined air flow rate is selected from a predetermined air flow range in accordance with at least one of:
   a desired parameter of transformation of said at least one portion of the first plurality of undesirable impurities into said at least one oxidation product, and
   the properties of said at one first transitional heterogeneous catalyst.

6. The method of claim 5, wherein said predetermined air flow ranges from about 0.1 h-1 to about 80 h-1.

7. The method of claim 1, wherein said first transitional heterogeneous catalyst further comprises a support selected from a group comprising: a neutral support and an acidic support.

8. The method of claim 1, wherein said first transitional heterogeneous catalyst further comprises at least one support selected from a group comprising: carbonic sorbents, neutral forms of aluminum oxide, neutral forms of aluminum salts, salts of metals of the main subgroup of group II metals of the Periodic table, coals, unreactive aluminum hydroxide, unreactive magnesia; carbonates, sulfates and phosphates of metals of groups II and III of the Periodic table, and calcium phosphate that has been prepared to comprise a crystalline phase represented predominantly by a substantial quantity of hydroxyapatite.

9. The method of claim 1, wherein said second heterogeneous catalyst comprises at least one heterogeneous catalyst selected from a group comprising: zeolites, combination of aluminosilicate contacts on the base of X or Y type zeolites or other types of zeolites, any sulfo-ion exchange resins of the type Amberlyst, Amberlite, Lewatit, sulphuric acid, Wofatit, KU-23, sulfonic acid, cation exchange resin acidic catalyst having a general static, exchange capacity of at least about 1 mmole/cm$^3$ and a working temperature interval of about 80° C. to about 155° C., higher porosity aluminosilicates, promoted medium and higher porosity aluminosilicates, and modified medium and higher porosity aluminosilicates.

10. The method of claim 1, wherein said second heterogeneous catalyst comprises a pore entrance size greater than about 5 Angstroms.

11. The method of claim 1, wherein said first predetermined operating conditions are selected and configured such that oxidation and separation of said plural impurities occurs at a first reaction rate, sufficiently greater than a second reaction rate of reaction between said plural impurities and the phenol, to prevent phenol oxidation and formation of additional undesirable substances.

12. The method of claim 1, wherein said first predetermined operating conditions comprise conducting said step (a) within a first reaction temperature range, and wherein said second predetermined operating conditions comprise conducting said step (b) within a second reaction temperature range.

13. The method of claim 12, wherein said first and said second reaction temperature ranges are each within about 50° C. to about 250° C.

14. The method of claim 12, wherein said second reaction temperature range is higher than said first reaction temperature range.

15. The method of claim 1, further comprising the step of:
   (f) after said step (a), and before said step (b), selectively returning at least a portion of a partially treated phenol product of said step (a), to said first step for additional treatment thereof.

16. The method of claim 1, further comprising the step of:
(g) after said step (b); selectively returning at least a portion of a treated phenol product of said step (b), to at least one of said step (a) and said step (b), for additional treatment thereof.

17. The method of claim 1, wherein the predetermined plurality of undesirable impurities comprise a plurality of impurities selected from a group comprising: alpha-methyl styrene (AMS), mesityl oxide (MO), phorone, 2-methylbenzofuran (2-MBF), cresols, and other alkylaromatic, unsaturated and carbonyl-containing compounds.

18. The method of claim 1, wherein said first transitional heterogeneous catalyst comprises a plurality of transitional heterogeneous catalysts.

19. The method of claim 1, Wherein said first transitional heterogeneous catalyst comprises a plurality of transitional valency metals.

20. The method of claim 1, wherein said second heterogeneous catalyst comprises a plurality of heterogeneous catalysts different from said first transitional heterogeneous catalyst.

21. The method of claim 2, wherein said first reactor comprises a first plurality of reactors.

22. The method of claim 2, wherein said second reactor comprises a second plurality of reactors.

* * * * *